United States Patent [19]

Stolowitz

[11] Patent Number: 5,623,055

[45] Date of Patent: Apr. 22, 1997

[54] PHENYLBORONIC ACID COMPLEXES DERIVED FROM AMINOSALICYLIC ACID FOR BIOCONJUGATE PREPARATION

[75] Inventor: Mark L. Stolowitz, Long Beach, Calif.

[73] Assignee: Prolinx, Inc., Redmond, Wash.

[21] Appl. No.: 189,176

[22] Filed: Jan. 28, 1994

[51] Int. Cl.⁶ ................................................. C07F 5/02
[52] U.S. Cl. .................. 530/391.1; 424/450; 530/345; 530/350; 530/341.7; 530/402; 558/288; 558/289
[58] Field of Search ...................... 558/288, 289; 424/450; 530/345, 350, 391.1, 391.7, 402

[56] References Cited

U.S. PATENT DOCUMENTS 2,548,257  7/1951  Goldberg et al. .
4,269,605  5/1981  Dean et al. .
4,281,181  7/1981  Nagasawa et al. .

(List continued on next page.)

FOREIGN PATENT DOCUMENTS 9013818  11/1990  WIPO .
9208722   5/1992  WIPO .
9420858   9/1994  WIPO .

OTHER PUBLICATIONS

Borrebaeck, Journal of Immunological Methods, vol. 123, pp. 157–165 (1989).

Wilcheck, M. & Bayer, E.A.; "Introduction to Avidin–Biotin Technology"; *Methods in Enzymology*; vol. 184; 1990 (USA).

(List continued on next page.)

*Primary Examiner*—Richard L. Raymond
*Attorney, Agent, or Firm*—Blakely, Sokoloff, Taylor & Zafman

[57] ABSTRACT

The present invention relates to a novel class of bioconjugates derived from phenylboronic acid complexes, and the method of making and using such bioconjugate complexes. The complexes are in the form of the following general formulas.

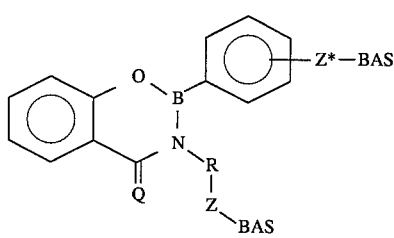

General Formula I

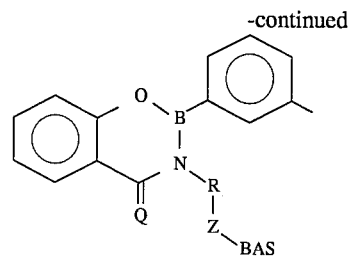

General Formula II

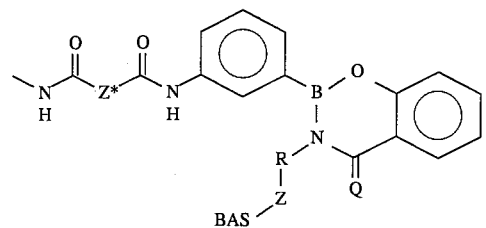

General Formula III

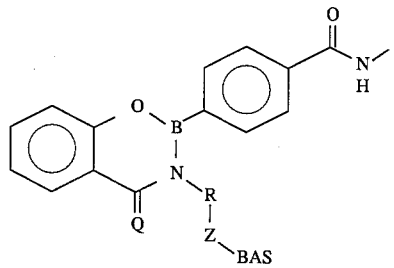

General Formula IV

General Formula V

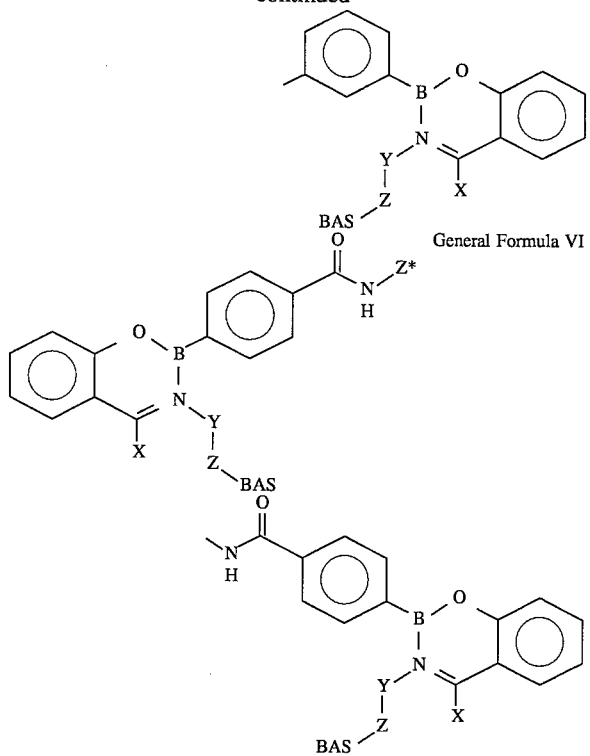

General Formula VI wherein group Q is selected from either O, S, NH, N-alkyl and N-aryl, wherein alkyl denotes a hydrocarbon moiety, wherein aryl is selected from either an aromatic ring, a substituted aromatic ring and fused aromatic rings, wherein group R is preferably selected from either O, NH, $CH_2$, alkyl and aryl, wherein alkyl and aryl are as were previously defined, wherein group X is selected from either H, $CH_3$ and $C_6H_5$, wherein group Y is selected from either O, NH, $CH_2$, alkyl and aryl, wherein alkyl and aryl are as were previously defined, wherein groups Z and Z* comprises spacers selected from either alkyl and polyethyleneglycol chains, of from 1 to 16 carbon equivalents in length, wherein the chain may contain intermediate amide and disulfide bonds, and wherein groups Z and Z* are preferably selected from, but not limited to, either $(CH_2)_n$, wherein n=1 to 5, and $(CH_2CH_2O)_{n'}$, wherein n'=2 to 4, and wherein groups BAS and BAS* are bioactive species.

2 Claims, 9 Drawing Sheets

U.S. PATENT DOCUMENTS

| | | | |
|---|---|---|---|
| 4,496,722 | 1/1985 | Gallop et al. | |
| 4,713,346 | 12/1987 | Gallop et al. | |
| 4,783,487 | 11/1988 | Brune. | |
| 4,851,443 | 7/1989 | Brune. | |
| 4,894,229 | 1/1990 | Polson et al. | |
| 4,910,300 | 3/1990 | Urdea et al. | |
| 5,002,883 | 3/1991 | Bieniarz et al. | |
| 5,045,451 | 9/1991 | Uhr et al. | 435/7.23 |
| 5,093,232 | 3/1992 | Urdea et al. | |
| 5,183,653 | 2/1993 | Linder et al. | |
| 5,242,842 | 9/1993 | Sundrehagen | 436/536 |

OTHER PUBLICATIONS

Kessler et al.; "Non-radioactive Labeling and Detection of Nucleic Acids"; *Biol. Chem. Hoppe-Seyler*; vol. 371, pp. 917–927; 1990 (USA).

Singhal, R.P. & DeSilva, S.S.M.; "Boronate Affinity Chromatography"; *Advances in Chromatography*; vol. 31, pp. 293–335; 1992 (USA).

Mazzeo, J.R. & Krull, I.S.; "Immobilized Boronates for the Isolation and Separation of Bioanalytes"; *Biochromatography*; vol. 4, pp. 124–130; 1989.

Bergold, A. & Scouten, W.H.; "Borate Chromatography"; *Solid Phase Biochemistry*; Ch. 4, pp. 149–187; 1983 (USA).

Lorand, J.P. & Edwards, J.O.; "Polyol Complexes and Structure of the Benzeneboronate Ion"; *J. Org. Chem.*; vol. 24, p. 769; 1959 (USA).

Bowie, R.A. & Musgrave, O.C.; "Organoboron Compounds. Part V.* The Hydrolysis of Cyclic Phenylboronates"; *J. Amer. Chem. Soc.*; pp. 3945–3949; 1963 (USA).

Sienkiewicz, P.A. & Roberts, D.C.; "pH Dependence of Boronic Acid–Diol Affinity in Aqueous Solution"; *J. Inorg. Nucl. Chem.*; vol. 42, pp. 1559–1571; 1980 (USA).

Tanner, D.W. & Bruice, T.C.; "Boric Acid Esters" *J. Amer. Chem. Soc.*; vol. 89, pp. 6954–6971; 1967 (USA).

Kliegel, W. & Nanninga, D.; "Borchelate von Salicylaldoxim und Derivaten"; *Monatshefte Fur Chemie*; vol. 114, pp. 465–484; 1983 (FRG).

Imagawa et al.; "Characteristics and Evaluation of Antibody–Horseradish Peroxidase Conjugates, etc."; *J. Applied Biochemistry*; vol. 4, pp. 41–57; 1982 (USA).

Kessler, C.; *Advances in Mutagenesis Research* (Obe, G. ed.); pp. 105–152; Springer–Verlag, Berlin/Heidelberg; 1990 (USA).

Brinkley, M.; "A Brief Survey of Methods for Preparing Protein Conjugates with Dyes, Haptens, and Cross Linking Reagents"; *Bioconjugate Chem.*; vol. 3; pp. 2–13; 1992 (USA).

Linder et al.; "Technetium Labeling of Monoclonal Antibodies with Functionalized BATOs 1. TcCl(DMG)$_3$PITC"; *Bioconjugate Chem.*; vol. 2, pp. 160–170; 1991 (USA).

Linder et al.; "Technetium Labeling of Monoclonal Antibodies with Functionalized BATOs 2. TcCl(DMG)$_3$CPITC Labeling of B72.3, etc." *Bioconjugate Chem.*; vol. 2, pp. 407–415; 1991(USA).

Burnett et al.; "Synthesis of a Fluorscent Boronic Acid Which Reversibly Binds to Cell Walls, etc."; *Biochem. Biophys. Research Commun.*; vol. 96, pp. 157–162; 1980 (USA).

Steinberg, G.M. & Swidler, R.; "The Benzohydroxamate Anion"; *J. Org. Chem. Vol.*; vol. 30, pp. 2362–2365; 1965 (USA).

Bauer, L. & Exner, O.; "The Chemistry of Hydroxamic Acids and N–Hydroxyimides"; *Angew. Chem. Internat. Edit.*; vol. 13, pp. 376–384; 1974 (USA).

Cai, S.X. & Kean, J.; "o–Acetomidophenylboronate Esters Stabilized Toward Hydrolysis by an Intramolecular O–B Interation, etc."; *Bioconjugate Chem.*; vol. 2, pp. 317–322; 1991 (USA).

Ramalingam, K. & Nowotnik, D.; "Syntheses of Some Isothiocyanatophenylboronic Acids"; *Org. Prep. Proc. Int.*; vol. 23, 729–734; 1991 (USA).

Kliegel, W. & Nanninga, D.; "Borchelate Von Salicylade-hydnitronen"; *Journal of Organometallic Chem.*; vol. 243, pp. 373–385; 1983 (USA).

Roberts et al.; "Pluripotential Amino Acids"; *Tetrahedron Letters*; vol. 21, pp. 3435–3438; 1980 (USA).

Kemp, D.S. & Roberts, D.; "New Protective Groups for Peptide Synthesis—II The DOBZ Group, etc."; *Tetrahedron Letters*; vol. 52, pp. 4629–4632; 1975 (USA).

Kliegel, W. & Nanninga, D.; "Borchelate von N–substituierten Hydroxamsauren"; *Chem. Ber.*; vol. 116, pp. 2616–2629; 1983 (FRG).

Mikesova, M. & Bartusek, M.; "Reaction of Boric Acid with Salicylic and Chromotropic Acids and with Their Derivatives"; *Chem. Zvesti*; vol. 32(4), pp. 472–477; 1978.

Feeney, R.E., "Chemical Modification of Proteins: Comments and Perspectives"; *Int. J. Peptide Protein Res.*; vol. 29, pp. 145–161 (USA), 1987.

Means, G.E. & Feeney, R.E.; "Chemical Modifications of Proteins: History and Applications"; *Bioconjugate Chem.*; vol. 1, pp. 2–12 (USA), 1990.

O'Shannessy, D.J. & Quarles, R.H.; "Labeling of the Oligosaccharide Moieties of Immunoglobulins"; *J. Immunological Methods*; vol. 99, pp. 153–161 (1987)(USA).

van't Reit, B., Wampler, G.L., & Elford, H.L.; "Synthesis of Hydroxy–and Amino–Substituted Benzohydroxamic Acids, etc."; *J. Medicinal Chem.*; vol. 22, No. 5, 589–92, 1979 (USA).

Soundararajan, et al.; "Boronic Acids for Affinity Chromatography: Spectral Methods for Determination, etc."; *Analytical Biochem.*; vol. 178, pp. 125–134, 1989 (USA).

Goodchild, J.; "Conjugates of Oligonucleotides and Modified Oligonucleotides: A Review of Their Synthesis and Properties"; *Bioconjugate Chem.*; vol. 1, No. 3, pp. 165–193, 1990 (USA).

Kessler, C.; *Nonradioactive Labeling and Detection of Biomolecules*; Ch. 1–3, 1992 (USA).

Meares, C.F., "Editorial; Introduction to Bioconjugate Chemistry"; *Bioconjugate Chem.*; vol. 1, No. 1, 1990 (USA).

Waggoner, A.S.; "Fluorescent Probes for Cytometry"; *Flow Cytometry and Sorting*; 2nd ed; pp. 209–225; 1990 (USA).

Chen, et al.; "Structure–Activity Relationships in a Series of 5–[(2,5–Dihydroxybenzyl) amino]salicylate, etc."; Chemical Abstracts; vol. 120; 322877v; 1994 (USA).

Hirano, et al.; "Silver halide color photographic material"; Chemical Abstracts; vol. 116; 140012u; 1992 (USA).

Kawasaki, et al.; "Silver halide photographic material with improved storage stability"; Chemical Abstracts; vol. 109; 160505r; 1988 (USA).

Priewe, H., et al.; "o–Hydroxybenzohydroxamic Acids"; Chemical Abstracts; vol. 52; 10184; 1958 (USA).

GENERAL FORMULA VII

GENERAL FORMULA VIII

↓ + BAS

↓ + BAS*

PHENYLBORONIC ACID
COMPLEXING SEMICONJUGATE

PHENYLBORONIC ACID
SEMICONJUGATE

GENERAL FORMULA I

GENERAL FORMULA VII

↓ + 2BAS

PHENYLBORONIC ACID
COMPLEXING SEMICONJUGATE

+

GENERAL FORMULA IX

→

GENERAL FORMULA II

GENERAL FORMULA VII

↓ + 2BAS

PHENYLBORONIC ACID COMPLEXING SEMICONJUGATE

+

GENERAL FORMULA X

→

GENERAL FORMULA III

GENERAL FORMULA XI

GENERAL FORMULA VIII

↓ + BAS

↓ + BAS*

PHENYLBORONIC ACID COMPLEXING SEMICONJUGATE

PHENYLBORONIC ACID SEMICONJUGATE

GENERAL FORMULA IV

GENERAL FORMULA XI

↓ +2BAS

PHENYLBORONIC ACID COMPLEXING SEMICONJUGATE

+

GENERAL FORMULA IX

→

GENERAL FORMULA V

GENERAL FORMULA XI

↓ + 2BAS

PHENYLBORONIC ACID COMPLEXING SEMICONJUGATE

GENERAL FORMULA X

GENERAL FORMULA VI

PHENYLBORONIC ACID COMPLEXES DERIVED FROM AMINOSALICYLIC ACID FOR BIOCONJUGATE PREPARATION

FIELD OF THE INVENTION

The present invention relates to the field of bioconjugate preparation, and more particularly, to a class of phenylboronic acid complexes useful for the conjugation of biological macro-molecules, and the method of making and using such complexes.

BACKGROUND OF THE INVENTION

Bioconjugation is a descriptive term for the joining of two or more different molecular species by chemical or biological means, in which at least one of the molecular species is a biological macromolecule. This includes conjugation of proteins, peptides, polysaccharides, lectins, hormones, nucleic acids, liposomes and cells, with each other or with any other molecular species that add useful properties, including radionuclides, toxins, haptens, inhibitors, fluorophores, ligands, etc. Immobilization of biological macromolecules is also considered a special case of bioconjugation in which the macromolecule is conjugated, either reversibly or irreversibly, to an insoluble support. Bioconjugation is utilized extensively in biochemical, immunochemical and molecular biological research. Applications of bioconjugation are numerous, and include affinity chromatography, affinity cytochemistry, histochemistry, pathological probe detection, diagnostics, signal amplification, immunoassay, hybridoma technology, blotting technology, bioaffinity sensors, gene probe detection, cross-linking reagents, affinity targeting, affinity perturbation, drug delivery, fusogenic reagents, immobilizing reagents, selective retrieval, selective elimination, flow cytometry and cytological probe detection.

AVIDIN-BIOTIN SYSTEM

Although numerous methods of bioconjugate preparation have been described, a significant number of those reported in the literature have been prepared by exploiting the Avidin-Biotin system, in which, the binding specificity of the protein Avidin (purified from egg white), or Streptavidin (purified from the bacterium *Streptomyces avidinii*), toward the cofactor Biotin (vitamin H) is utilized to bridge an Avidin conjugated macromolecule with a biotinylated macromolecule. Both Avidin and Streptavidin possess four Biotin binding sites of very high affinity ($K=10^{15}$ mol$^{-1}$). This system has been utilized extensively for enzyme-linked immuno solid-phase assay (ELISA), in which an enzyme-Avidin conjugate (useful for detection by reaction with the enzyme's substrate to afford a colored or chemiluminescent product) is employed to detect the presence of a biotinylated antibody, after first binding the antibody to an immobilized antigen or hapten. Applications of the Avidin-Biotin system number in the hundreds, and have recently been reviewed (Wilchek, M. and Bayer, E. A. (1990) *Methods in Enzymology*, 184). Although utilized extensively, several limitations are known to be associated with the Avidin-Biotin system, which include nonspecific binding generally attributed to the basicity of the Avidin molecule, nonspecific binding attributed to the presence of carbohydrate residues on the Avidin molecule, and background interference associated with the presence of endogenous Biotin, which is ubiquitous in both eukaryotic and prokaryotic cells.

DIGOXIGENIN ANTI-DIGOXIGENIN SYSTEM

An alternative bioconjugation system designed to overcome the limitations associated with the Avidin-Biotin system has recently been developed for the detection of gene probes by ELISA (Kessler, C., Höltke, H.-J., Seibl, R., Burg, J. and Mühlegger, K. (1990) *Biol. Chem. Hoppe-Seyler*, 371,917–965). This system involves the use of the steroid hapten Digoxigenin, an alkaloid occurring exclusively in Digitalis plants, and Fab fragments derived from polyclonal sheep antibodies against Digoxigenin (anti-Digoxigenin). The high specificity of the various anti-Digoxigenin antibodies affords low backgrounds and eliminates the nonspecific binding observed in Avidin-Biotin systems. Digoxigenin-labeled DNA and RNA probes can detect single-copy sequences in human genomic Southern blots. The development of the Digoxigenin anti-Digoxigenin system has recently been reviewed (Kessler, C. (1990) in Advances in Mutagenesis Research (Obe, G. ed.) pp. 105–152, Springer-Verlag, Berlin/Heidelberg).

IMMOBILIZED BORONATES

Phenylboronic acids are known to interact with a wide range of polar molecules having certain requisite functionalities. Complexes of varying stability, involving 1,2-diols, 1,3-diols, 1,2-hydroxy acids, 1,3-hydroxy acids, 1,2-hydroxylamines, 1,3-hydroxylamines, 1,2-diketones and 1,3-diketones, are known to form with either neutral phenylboronic acid or phenylboronate anion. Consequently, immobilized phenylboronic acids have been exploited as chromatographic media to selectively retain, from diverse biological samples, those molecular species having the requisite functionalities. Many important biological molecules including carbohydrates, catecholamines, prostaglandins, ribonucleosides, and steroids contain the requisite functionalities, and have been either analyzed or purified in this manner. The use of phenylboronic acid chromatographic media for the isolation and separation of various analytes has been reviewed (Singhal, R. P. and DeSilva, S. S. M. (1989) *Adv. Chromatog.*, 4, 124–130; Mazzeo, J. R. and Krull, I. S., *BioChromatog.*, 4, 124–130 (1989); and Bergold, A. and Scouten, W. H. (1983) in Solid Phase Biochemistry (Scouten, W. H. ed.) pp. 149–187, John Wiley & Sons, New York).

Phenylboronic acid, like boric acid, is a Lewis acid, and ionizes not by direct deprotonation, but by hydration to give the tetrahedral phenylboronate anion ($pK_a=8.86$). Phenylboronic acid is three times as strong an acid as boric acid. Ionization of phenylboronic acid is an important factor in complexation, in that, upon ionization, boron changes from trigonal coordination (having average bond angles of 120° and average bond lengths of 1.37 Å) to the tetrahedrally coordinated anion (having average bond angles of 109° and average bond lengths of 1.48 Å).

A number of phenylboronic acids have been described in the literature for use in preparation of immobilized phenylboronic acid chromatographic supports. Several of these compounds and their corresponding $pK_a$ values are illustrated below. Contemporary research in this field is directed toward the development of phenylboronic acids with $pK_a$ values below that of (3-aminophenyl)boronic acid ($pK_a$ 8.75), which is presently utilized in the preparation of all commercial phenylboronic acid chromatographic supports. The development on an immobilized phenylboronic acid chromatographic support with a significantly lower $pK_a$ than that of (3-aminophenyl)boronic acid would enable the retention of a variety of biomolecules under physiological conditions (pH 7.2), thereby substantially extending the breath of compounds suitable for analysis by the method.

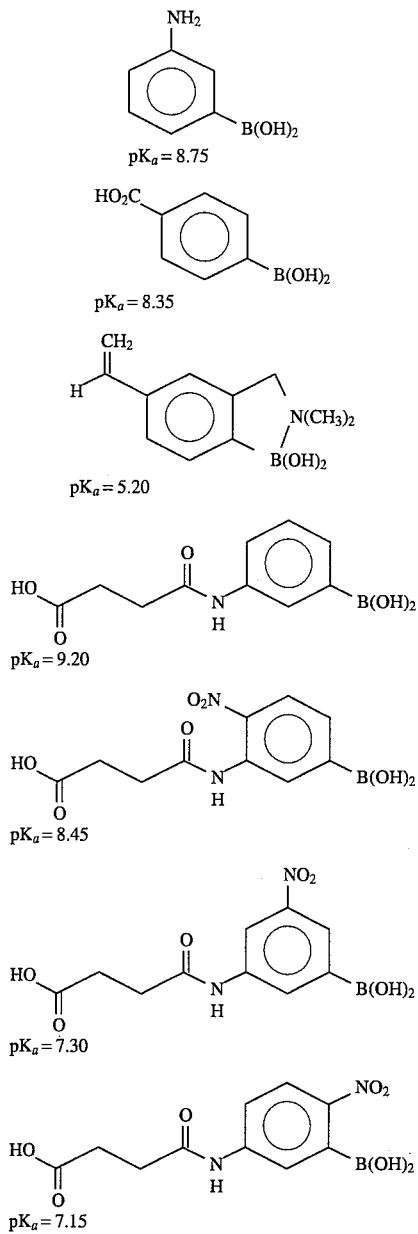

Compounds having cis or coaxial 1,2-diol and 1,3-diol functionalities, and particularly carbohydrates, are presently known to complex with immobilized phenylboronate anion, to form cyclic esters, only under alkaline aqueous conditions (Lorand, J. P. and Edwards, J. O. (1959) *J. Org. Chem.* 24, 769).

Acidification of 1,2-diol and 1,3-diol complexes is known to release the diol containing species, presumably due to hydrolysis of the cyclic ester, which is induced by ring-strain associated with a five-membered cyclic boronic acid ester involving trigonally coordinated boron. Coplaner aromatic 1,3-diols, like 1,8-dihydroxynaphthalene, are known to complex even under acidic conditions due to the hydrolytic stability of six-membered cyclic boronic acid esters (Sienkiewicz, P. A. and Roberts, D. C. (1980) *J. Inorg. Nucl. Chem.*, 42, 1559–1571).

Substituted phenols having pendant 1,3-hydroxylamide, 1,3-hydroxyamidine and 1,3-hydroxyoxime moieties are also known to complex reversibly with borate buffer, under alkaline aqueous conditions (Tanner, D. W. and Bruice, T. C. (1967) *J. Amer. Chem. Soc.*, 89, 6954–6971), in a manner analogous to that in which phenylboronic acids are known to complex.

Although immobilized phenylboronates have been utilized for chromatographic separation of biological molecules having the requisite functionalities, notwithstanding the substantial amount of research into bioconjugation, and the substantial amount of investment in this field, the selectivity of phenylboronic acid has not heretofore been exploited to enable the conjugation of biological macromolecules with one another or with other molecular species that add useful properties.

SUMMARY OF THE INVENTION

Definitions

As used herein the following terms have the following meanings:

Bioactive species refers to a compound preferably selected from, but not limited to, either proteins, peptides, polysaccharides, hormones, nucleic acids, liposomes, cells, drugs, radionuclides, toxins, haptens, inhibitors, fluorophores, ligands and solid-phase supports. Bioactive species are collectively those species which confer biological activity or detection capabilities upon bioconjugates.

Phenylboronic acid complexing reagent refers to a reagent comprised of a phenylboronic acid complexing moiety and a reactive moiety suitable for appending a phenylboronic acid complexing moiety to a bioactive species (see FIGS. 1 through 3, General Formula VII and FIGS. 4 through 6, General Formula XI). Phenylboronic acid complexing reagents are described in greater detail in my copending application "Phenylboronic Acid Complexing Reagents", Ser. No. 08/188,460, filed Jan. 28, 1994, and pending before the United States Patent and Trademark Office.

Phenylboronic acid reagent refers to a reagent comprised of a phenylboronic acid moiety and a reactive moiety suitable for appending a phenylboronic acid moiety to a bioactive species (see FIGS. 1 and 4, General Formula VIII).

Phenylboronic acid cross-linking reagent refers to a reagent comprised of two phenylboronic acid moieties separated by a spacer (see FIGS. 2 and 5, General Formula IX, and FIGS. 3 and 6, General Formula X).

Phenylboronic acid complexing semiconjugate refers to a bioactive species having a pendant phenylboronic acid complexing moiety which is derived from the reaction of a bioactive species with a phenylboronic acid complexing reagent (see FIGS. 1 through 6).

Phenylboronic acid semiconjugate refers to a bioactive species having a pendant phenylboronic acid moiety which is derived from the reaction of a bioactive species with a phenylboronic acid reagent (see FIGS. 1 and 4).

Bioconjugate complex refers to the product formed upon reaction of a phenylboronic acid complexing semiconjugate with a phenylboronic acid semiconjugate (see FIGS. 1 and 4, General Formulas I and IV, respectively) or the product formed upon reaction of a phenylboronic acid complexing semiconjugate with a phenylboronic acid cross-linking reagent (see FIGS. 2, 3, 5 and 6, General Formulas II, III, V and VI, respectively).

The present invention relates to a novel class of bioconjugates derived from phenylboronic acid complexes, and the method of making and using such bioconjugate complexes. In the present invention, in the place of prior art Avidin-Biotin and Digoxigenin-anti-Digoxigenin systems, phenylboronic acid complexes are utilized to facilitate chemical conjugation of bioactive species without the use of intermediary biological macromolecules. Bioconjugate complexes suitable for conjugation of two or more bioactive species, for the purpose of preparing bioconjugates, are selected from either General Formulas I through VI, set forth below.

16 carbon equivalents in length, wherein either chain may contain intermediate amide and disulfide bonds, wherein Z and Z* may be the same or different, and wherein groups BAS and BAS* are different bioactive species.

Bioconjugate complexes of General Formula I are preferably those wherein group Q is selected from, but not limited to, either O, NH and $NC_6H_5$, wherein group R is preferably selected from, but not limited to, either O and $CH_2$, wherein groups Z and Z* are preferably selected from, but not limited to, either $(CH_2)_n$, wherein n=1 to 5, and $(CH_2CH_2O)_{n'}$, wherein n'=2 to 4, and wherein BAS and BAS* are different bioactive species.

General Formula II

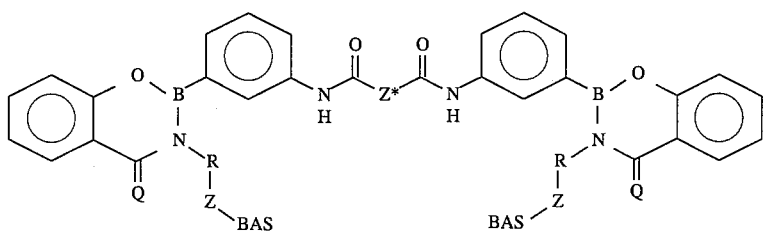

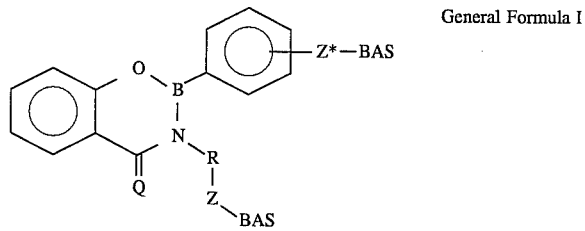

General Formula I

Bioconjugate complexes of General Formula I are those wherein group Q is selected from either O, S, NH, N-alkyl and N-aryl, wherein alkyl denotes an alkyl hydrocarbon moiety, wherein aryl is selected from either an aromatic ring, a substituted aromatic ring and fused aromatic rings, wherein group R is selected from either O, NH, $CH_2$, alkyl and aryl, wherein alkyl denotes a hydrocarbon moiety of from 2 to 6 carbons in length, wherein aryl is selected from either an aromatic ring, a substituted aromatic ring and fused aromatic rings, wherein groups Z and Z* comprise a spacer selected from either an alkyl of from 1 to 16 carbon equivalents in length and a polyethyleneglycol chain, up to Bioconjugate complexes of General Formulas II and III are those wherein group Q is selected from either O, S, NH, N-alkyl and N-aryl, wherein alkyl denotes an alkyl hydrocarbon moiety, wherein aryl is selected from either an aromatic ring, a substituted aromatic ring and fused aromatic rings, wherein group R is selected from either O, NH, $CH_2$, alkyl and aryl, wherein alkyl denotes a hydrocarbon moiety of from 2 to 6 carbons in length, wherein aryl is selected from either an aromatic ring, a substituted aromatic ring and fused aromatic rings, wherein groups Z and Z* comprise a spacer selected from either an alkyl of from 1 to 6 carbon equivalents in length and a polyethyleneglycol chain, up to 16 carbon equivalents in length, wherein either chain may contain intermediate amide and disulfide bonds, wherein Z* is appended to two phenylboronic acid moieties, and wherein group BAS is a bioactive species.

General Formula III

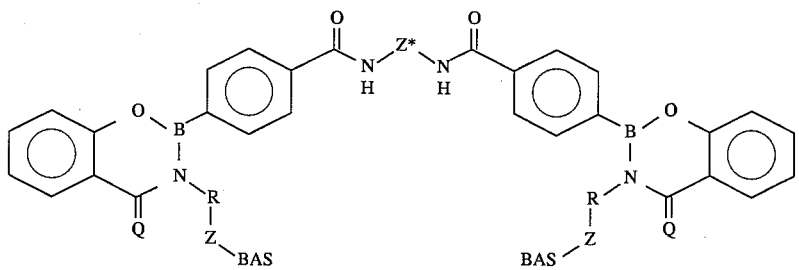

Bioconjugate complexes of General Formulas II and III are preferably those wherein group Q is selected from, but not limited to, either O, NH and $NC_6H_6$, $H_5$, wherein group R is preferably selected from, but not limited to, either O and $CH_2$, wherein groups Z and Z* are preferably selected from, but not limited to, either $(CH_2)$, wherein n=1 to 5, and $(CH_2CH_2O)_{n'}$, wherein n'=2 to 4, and wherein group BAS is a bioactive species.

General Formula IV

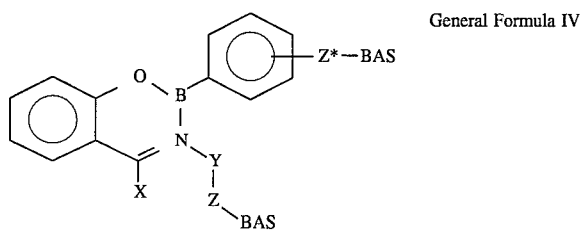

Bioconjugate complexes of General Formula IV are those wherein group X is selected from either H, $CH_3$ and $C_6H_5$, wherein group Y is selected from either O, NH, $CH_2$, alkyl and aryl, wherein alkyl denotes an alkyl hydrocarbon selected moiety, wherein aryl is from either an aromatic ring, a substituted aromatic ring and fused aromatic rings, wherein groups Z and Z* comprise a spacer selected from either an alkyl of from 1 to 16 carbon equivalents in length and a polyethyleneglycol chain, up to 16 carbon equivalents in length, wherein either chain may contain intermediate amide and disulfide bonds, wherein groups Z and Z* may be the same or different, and wherein groups BAS and BAS* are different bioactive species.

Bioconjugate complexes of General Formula IV are preferably those wherein group X is selected from, but not limited to, either H and $C_6H_5$, wherein group Y is preferably selected from, but not limited to, either O and $CH_2$, wherein groups Z and Z* are preferably selected from, but not limited to, either $(CH_2)_n$, wherein n=1 to 5, and $(CH_2CH_2O)_{n'}$, wherein n'=2 to 4, and wherein groups BAS and BAS* are different bioactive species.

General Formula V

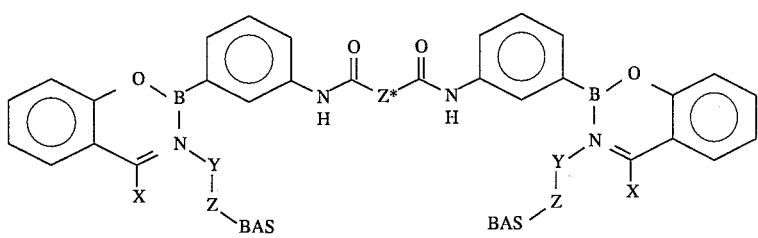

Bioconjugate complexes of General Formulas V and VI are those wherein group X is selected from either H, $CH_3$ and $C_6H_5$, wherein group Y is selected from either O, NH, $CH_2$, alkyl and aryl, wherein alkyl denotes an alkyl hydrocarbon moiety, wherein aryl is selected from either an aromatic ring, a substituted aromatic ring and fused aromatic rings, wherein groups Z and Z* comprise a spacer selected from either alkyl of from 1 to 16 carbon equivalents in length and a polyethyleneglycol chain up to 16 carbon equivalents in length, wherein either chain may contain intermediate amide and disulfide bonds, wherein group Z* is appended to two phenylboronic acid moieties, and wherein group BAS is a bioactive species.

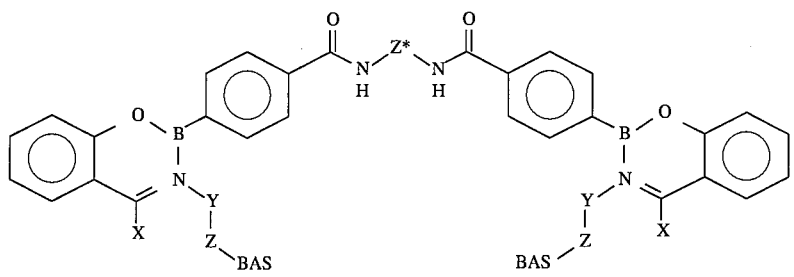

General Formula VI

Bioconjugate complexes of General Formulas V and VI are preferably those wherein group X is selected from, but not limited to, either H and $C_6H_5$, wherein group Y is preferably selected from, but not limited to, either O and $CH_2$, wherein groups Z and Z* are preferably selected from, but not limited to, either $(CH_2)_n$, wherein n=1 to 5, and $(CH_2CH_2O)_{n'}$, wherein n'=2 to 4, and wherein group BAS is a bioactive species.

Bioconjugate complexes of General Formulas I and IV are employed to conjugate two different bioactive species, for example, to conjugate an enzyme with an antibody for use in an ELISA assay, to conjugate a nucleic acid probe with a fluorophore to facilitate detection of a genomic sequence, and to conjugate a toxin to a monoclonal antibody for use in targeted drug delivery. Bioconjugate complexes of General Formulas I and IV comprise the most general application of the method of bioconjugate preparation described herein.

Bioconjugate complexes of General Formulas II, III, V and VI are employed to conjugate identical bioactive species by cross-linking bioactive species having pendant phenylboronic acid complexing moieties into macromolecular aggregates. Aggregates of this type involving enzymes are useful for increasing detection limits in ELISA and related assays by substantially increasing the effective concentration of enzyme available for conversion of colorless substrate into detectable product. Similarly, fluorophore labeled proteins having pendant phenylboronic acid complexing moieties my be aggregated in this manner to improve their visual or spectrophotometric detection. Aggregates having excess pendant phenylboronic acid moieties may be further conjugated with other bioactive species having pendant phenylboronic acid complexing moieties (phenylboronic acid complexing semiconjugates). This general approach is analogous to the preparation of sandwich type assays involving the Avidin Biotin system.

Phenylboronic acid cross-linking reagents of General Formulas IX and X (see FIGS. 2, 3, 5 and 6) may also be employed, by reaction in large excess, and subsequent removal of excess reagent, to convert bioactive species having pendant phenylboronic acid complexing moieties (phenylboronic acid complexing semiconjugates) into bioactive species having pendant phenylboronic acid moieties (phenylboronic acid semiconjugates).

Bioconjugate complexes of General Formulas I through VI are prepared in either buffered aqueous solutions, organic solvents and aqueous solutions containing organic solvents. The complex is formed within a few minutes at room temperature. Preparation of the bioconjugate complex is insensitive to significant variations in ionic strength, temperature, and the presence of chaotropic agents (protein denaturants), which are incompatible with prior art systems wherein the structure of a biological macromolecule must be maintained to preserve requisite binding properties. In most instances, the constraints governing the formation of bioconjugate complexes, by the system described herein, are limited to the selection of an appropriate pH and whatever additional limitations are imposed by the conditions required to maintain viability of the bioactive species.

DETAILED DESCRIPTION OF THE INVENTION

Preparation of Bioconjugate Complexes

Figure 1:
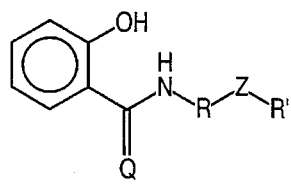
FIG. 1 illustrates the preparation of bioconjugate complexes of General Formula I.
Figure 1:
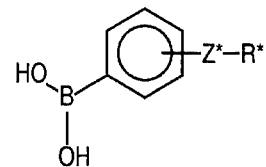
Figure 1:
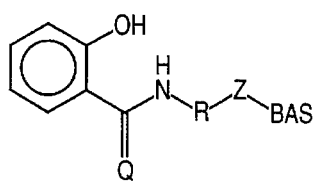
Figure 1:
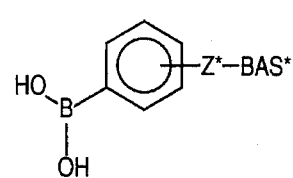
Figure 1:
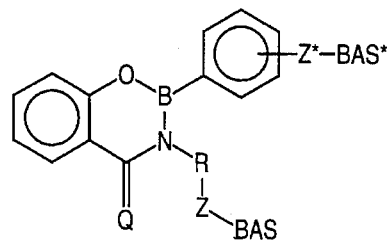

As illustrated in FIG. 1, bioconjugate complexes of General Formula I are prepared by a three-step process in which:

(1) A phenylboronic acid complexing reagent of General Formula VII, derived from a compound preferably selected from either salicylic acid and dithiosalicylic acid, wherein group Q is selected from either O, S, NH, N-alkyl and N-aryl, wherein alkyl denotes an alkyl hydrocarbon moiety, wherein aryl is selected from either an aromatic ring, a substituted aromatic ring and fused aromatic rings, wherein group R is preferably selected from either O, NH, $CH_2$, alkyl and aryl, wherein alkyl and aryl are as were previously defined, wherein group Z comprises a spacer selected from either an alkyl of from 1 to 16 carbon equivalents in length and a polyethyleneglycol chain, up to 16 carbon equivalents in length, wherein either chain may contain intermediate amide and disulfide bonds, and wherein group Z is preferably selected from, but not limited to, either $(CH_2)_n$, wherein n=1 to 5, and $(CH_2CH_2O)_{n'}$, wherein n'=2 to 4, and wherein group R' is preferably selected from, but not limited to, either amino, hydrazide, thiol, isothiocyanate, bromoacetamide, iodoacetamide, maleimide N-hydroxysuccinimidyl ester and N-hydroxysulfosuccinimidyl ester moieties, is condensed with a bioactive species to prepare a phenylboronic acid complexing semiconjugate;

(2) A phenylboronic acid reagent of General Formula VIII, derived from a compound preferably selected from, but not limited to, either (3-aminophenyl)boronic acid and (4-carboxy-phenyl)boronic acid, wherein group Z* comprises a spacer selected from either an alkyl of from 1 to 16 carbon equivalents in length and a polyethyleneglycol chain, up to 16 carbon equivalents in length, wherein either chain may contain intermediate amide and disulfide bonds, and wherein group Z* is preferably selected from, but not limited to, either $(CH_2)_n$, wherein n=1 to 5, and $(CH_2CH_2O)_{n'}$, wherein n'=2 to 4, and wherein group R* is preferably selected from, but not limited to, either amino, hydrazide, thiol, isothiocyanate, bromoacetamide, iodoacetamide, maleimide N-hydroxysuccinimidyl ester and N-hydroxysulfosuccinimidyl ester moieties, is condensed with a bioactive species to prepare a phenylboronic acid semiconjugate;

(3) The phenylboronic acid complexing semiconjugate, prepared as described in (1) above, and the phenylboronic acid semiconjugate, prepared as described in (2) above, are reacted with one another to afford a bioconjugate complex of General Formula I, wherein BAS and BAS* are bioactive species, and wherein groups Q, R, Z and Z* are as were previously described.

Figure 2:
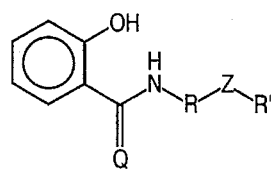
FIG. 2 illustrates the preparation of bioconjugate complexes of General Formula II.
Figure 2:
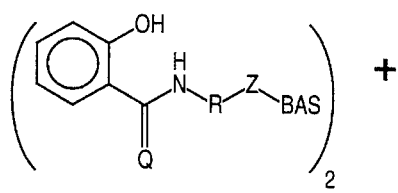
Figure 2:
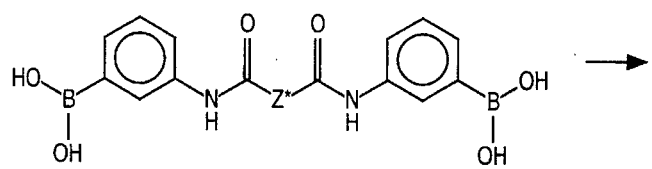
Figure 2:
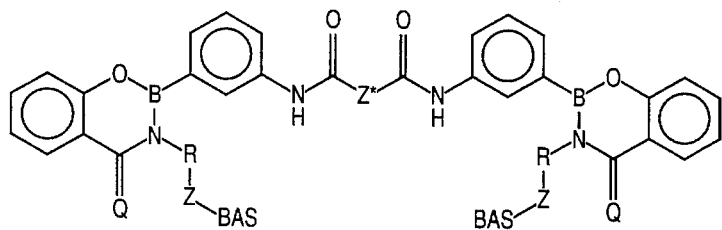

As illustrated in FIG. 2, bioconjugate complexes of General Formula II are prepared by a two-step process in which:

(1) A phenylboronic acid complexing reagent of General Formula VII, wherein groups Q, R, Z and R' are as were previously defined, is condensed with a bioactive species to prepare phenylboronic acid complexing semiconjugates;

(2) The phenylboronic acid complexing semiconjugates, prepared as described in (1) above, are reacted with a phenylboronic acid reagent (homobifunctional crosslinker) of General Formula IX, derived from (3-aminophenyl)boronic acid, wherein group Z* is as was previously defined, to afford a bioconjugate complex of General Formula II, wherein groups Q, R, Z, Z* and BAS are as were previously described.

Figure 3:
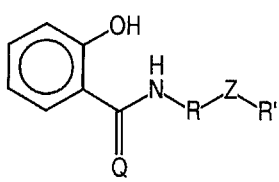
FIG. 3 illustrates the preparation of bioconjugate complexes of General Formula III.
Figure 3:
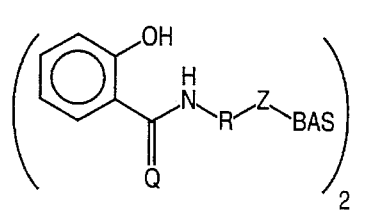
Figure 3:
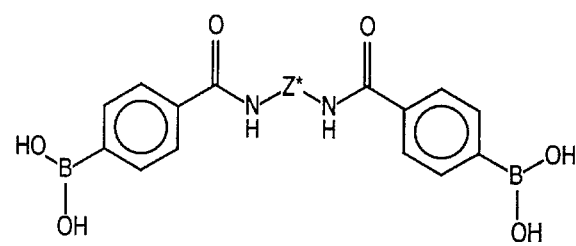
Figure 3:
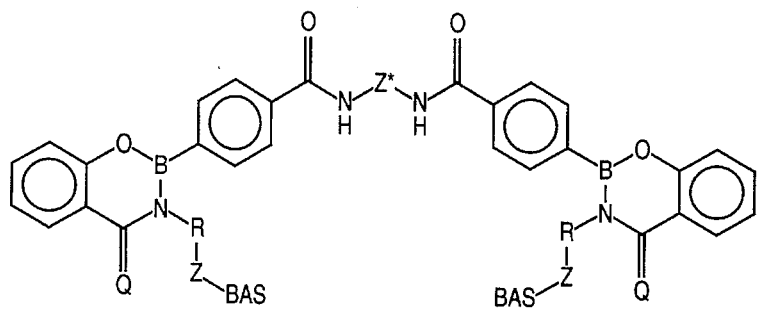

As illustrated in FIG. 3, bioconjugate complexes of General Formula III are prepared by a two-step process in which:

(1) A phenylboronic acid complexing reagent of General Formula VII, wherein groups Q, R, Z and R' are as were previously defined, is condensed with a bioactive species to prepare phenylboronic acid complexing semiconjugates;

(2) The phenylboronic acid complexing semiconjugates, prepared as described in (1) above, are reacted with a phenylboronic acid reagent (homobifunctional crosslinker) of General Formula X, derived from (4-carboxyphenyl)boronic acid, wherein group Z* is as was previously defined, to afford a bioconjugate complex of General Formula III, wherein groups Q, R, Z, Z* and BAS are as were previously described.

Figure 4:
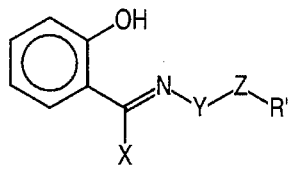
FIG. 4 illustrates the preparation of bioconjugate complexes of General Formula IV.
Figure 4:
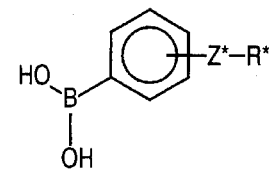
Figure 4:
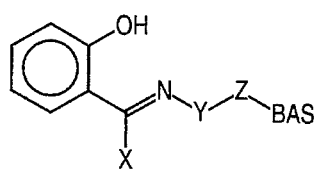
Figure 4:
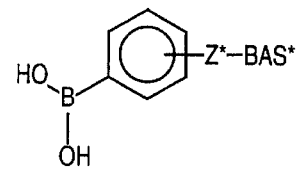
Figure 4:
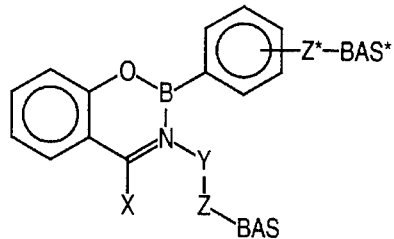

As illustrated in FIG. 4, bioconjugate complexes of General Formula IV are prepared by a three-step process in which:

(1) A phenylboronic acid complexing reagent of General Formula XI, derived from a compound preferably selected from either salicylaldehyde and 2'-hydroxyacetophenone, wherein group X is selected from either H, $CH_3$ and $C_6H_5$, wherein group Y is selected from either O, NH, $CH_2$, alkyl and aryl, wherein alkyl denotes a hydrocarbon chain, wherein aryl is selected from either an aromatic ring, a substituted aromatic ring and fused aromatic rings, wherein group Z comprises a spacer selected from either an alkyl and polyethyleneglycol chain, of from 1 to 16 carbon equivalents in length, wherein the chain may contain intermediate amide and disulfide bonds, and wherein group Z is preferably selected from, but not limited to, either $(CH_2)_n$, wherein n=1 to 5, and $(CH_2CH_2O)_{n'}$, wherein n'=2 to 4, and wherein group R' is preferably selected from, but not limited to, either amino, hydrazide, thiol, isothiocyanate, bromoacetamide, iodoacetamide, maleimide N-hydroxysuccinimidyl ester and N-hydroxysulfosuccinimidyl ester moieties, is condensed with a bioactive species to prepare a phenylboronic acid complexing semiconjugate:

(2) A phenylboronic acid reagent of General Formula VIII, derived from a compound preferably selected from, but not limited to, either (3-aminophenyl)boronic acid and (4-carboxyphenyl)boronic acid, wherein group Z* comprises a spacer selected from either an alkyl and polyethyleneglycol chain, of from 1 to 16 carbon equivalents in length, wherein the chain may contain intermediate amide and disulfide bonds, and wherein group Z* is preferably selected from, but not limited to, either $(CH_2)_n$, wherein n=1 to 5, and $(CH_2CH_2O)_{n'}$, wherein n'=2 to 4, and wherein group R* is preferably selected from, but not limited to, either amino, hydrazide, thiol, isothiocyanate, bromoacetamide, iodoacetamide, maleimide N-hydroxysuccinimidyl ester and N-hydroxysulfosuccinimidyl ester moieties, is condensed with a bioactive species to prepare a phenylboronic acid semiconjugate;

(3) The phenylboronic acid complexing semiconjugate, prepared as described in (1) above, and the phenylboronic acid semiconjugate, prepared as described in (2) above, are reacted with one another to afford a bioconjugate complex of General Formula IV, wherein BAS and BAS* are bioactive species, and wherein groups X, Y, Z and Z* are as were previously described.

Figure 5:
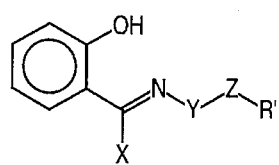
FIG. 5 illustrates the preparation of bioconjugate complexes of General Formula V.
Figure 5:
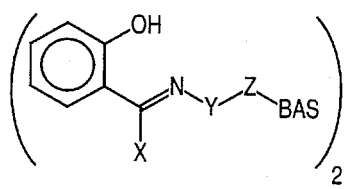
Figure 5:
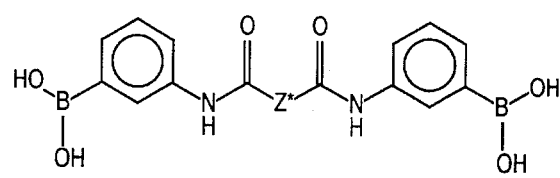
Figure 5:
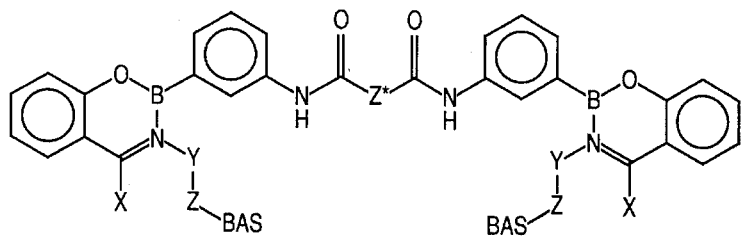

As illustrated in FIG. 5, bioconjugate complexes of General Formula V are prepared by a two-step process in which:

(1) A phenylboronic acid complexing reagent of General Formula XI, wherein groups X, Y, Z and R' are as were previously defined, is condensed with a bioactive species to prepare phenylboronic acid complexing semiconjugates;

(2) The phenylboronic acid complexing semiconjugates, prepared as described in (1) above, are reacted with a phenylboronic acid reagent (homobifunctional crosslinker) of General Formula IX, derived from (3-aminophenyl)boronic acid, wherein group Z* is as was previously defined, to afford a bioconjugate complex of General Formula II, wherein groups X, Y, Z, Z* and BAS are as were previously described.

Figure 6:
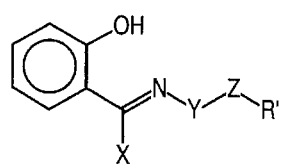
FIG. 6 illustrates the preparation of bioconjugate complexes of General Formula VI.
Figure 6:
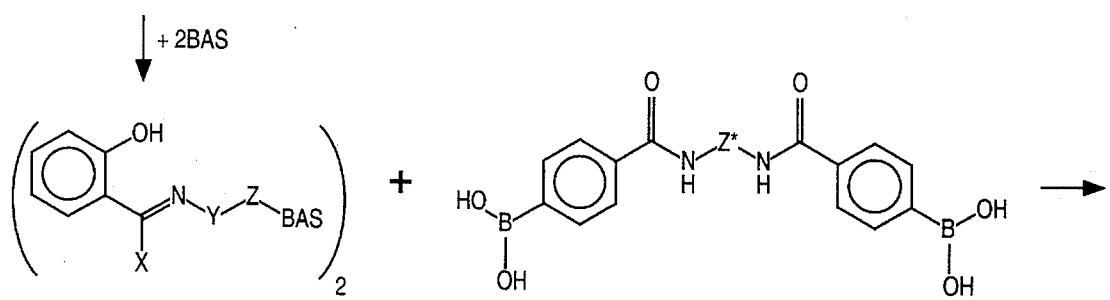
Figure 6:
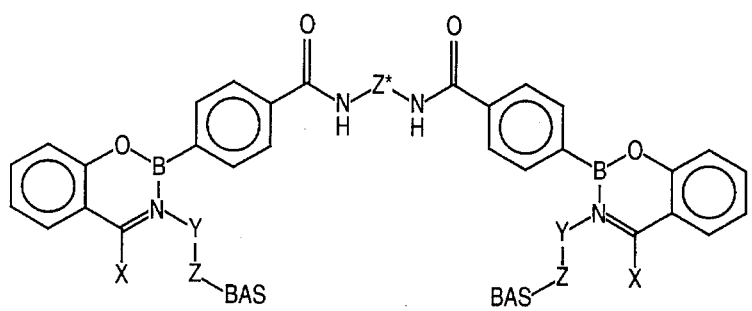

As illustrated in FIG. 6, bioconjugate complexes of General Formula VI are prepared by a two-step process in which:

(1) A phenylboronic acid complexing reagent of General Formula XI, wherein groups X, Y, Z and R' are as were previously defined, is condensed with a bioactive species to prepare phenylboronic acid complexing semiconjugates;

(2) The phenylboronic acid complexing semiconjugates, prepared as described in (1) above, are reacted with a phenylboronic acid reagent (homobifunctional crosslinker) of General Formula X, derived from (4-carboxyphenyl)boronic acid, wherein group Z* is as was previously defined, to afford a bioconjugate complex of General Formula VI, wherein groups X, Y, Z, Z* and BAS are as were previously described.

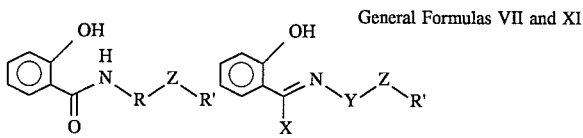

General Formulas VII and XI

Phenylboronic acid complexing reagents of General Formulas VII and XI are described in greater detail in my copending application "Phenylboronic Acid Complexing Regents", Ser. No. 188,460, filed Jan. 28, 1994, and pending before the United States Patent and Trademark Office.

Synthesis of Phenylboronic Acid Reagents of General Formula VIII

Figure 7:
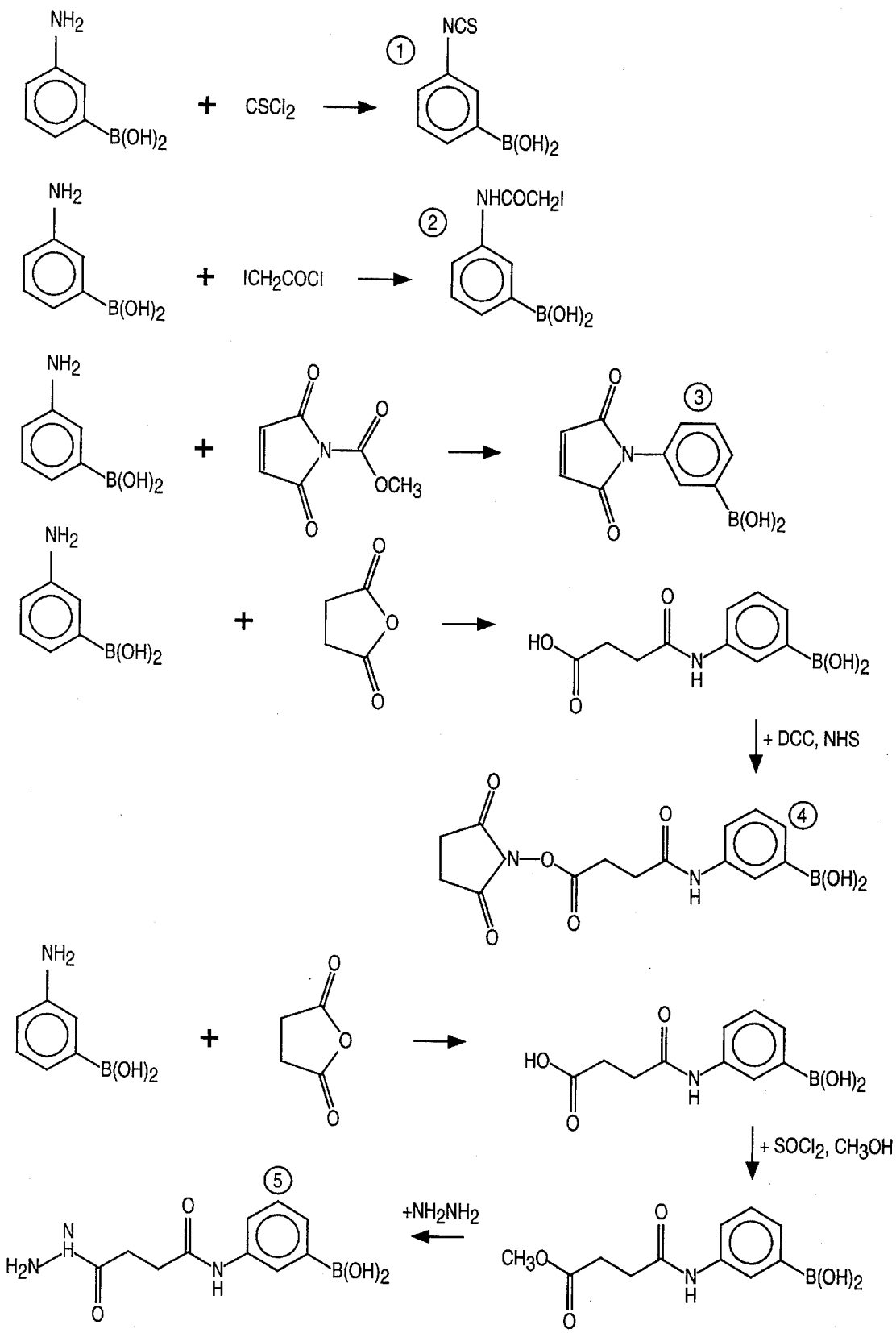
FIG. 7 illustrates the synthetic preparation of reagents of General Formula VIII.

The syntheses of phenylboronic acid reagents of General Formula VIII (see FIGS. 1 and 4) are set forth in FIG. 7.

Reagents of General Formula VIII are derived from a compound preferably selected from, but not limited to, either (3-aminophenyl)boronic acid, (4-carboxyphenyl)boronic acid and N-(6-nitro-3-dihydroxyborylphenyl)succinamic acid. Reagents of General Formula VIII are preferably selected from, but not limited to, either (3-isothiocyanatophenyl)boronic acid (FIG. 7, #1), (5-carboxy-3-isothiocyanatophenyl)boronic acid, (3-iodoacetamidophenyl)boronic acid (FIG. 7, #2), (3-maleimidophenyl)boronic acid (FIG. 7, #3), (3-dihydroxyborylphenyl)succinamic acid succinimidyl ester (FIG. 7, #4) and (3-dihydroxyborylphenyl)succinamic acid hydrazide (FIG. 7, #5). The synthetic preparation of (3-isothiocyanatophenyl)boronic acid and (5-carboxy-3-isothiocyanatophenyl)boronic acid has recently been reported (Linder, K. E., Wen, M. D., Nowotnik, D. P., Malley, M. F., Gougoutas, J. Z., Nunn, A. D. and Eckelman, W. C. (1991) *Bioconjugate Chem.*, 2, 160–170, and Linder, K. E., Wen, M. D., Nowotnik, D. P., Ramalingam, K., Sharkey, R. M., Yost, F., Narra, R. K., Nunn, A. D. and Eckelman, W. C. (1991) *Bioconjugate Chem.*, 2, 407–415).

Synthesis of Phenylboronic Acid Reagents of General Formulas IX & X

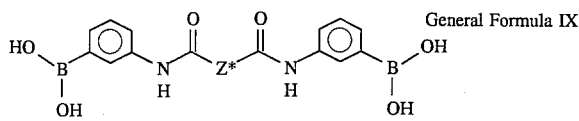

General Formula IX

Phenylboronic acid reagents of General Formula IX are prepared by condensation of (3-aminophenyl)boronic acid with an activated dicarboxylic acid preferably selected from, but not limited to, either succinyl chloride, adipoyl chloride, adiptic acid diisobutylcarbonate, suberoyl chloride,3,3'-dithiopropionyl chloride and 3,6,9-trioxaundecanedioyl chloride and 3,6,9-trioxaundecanedioic acid diisobutylcarbonate. The preparation of a single reagent of General Formula IX has been previously reported (Burnett, T. J., Peebles, H. C. and Hageman, J. H. (1980) *Biochem. Biophys. Research Commun.*, 96, 157–162).

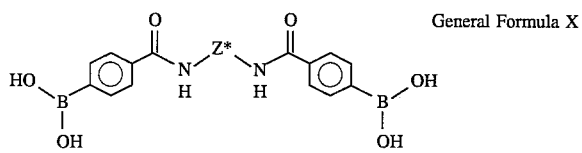

General Formula X

Phenylboronic acid reagents of General Formula X are prepared by activation of (4-carboxyphenyl)boronic acid with N,N-dicyclohexylcarbodiimide, followed by condensation with a diamine, preferably selected from, but not limited to, either 1,4-butanediamine, 1,6-hexanediamine and 2,2'-dithiodiaminoethane ($H_2NCH_2CH_2SSCH_2CH_2NH_2$).

Bioconjugate Complexes

Bioconjugate complexes of General Formulas I through VI are prepared in buffered aqueous solutions preferably selected from, but not limited to, acetate, citrate, phosphate and carbonate buffers. Borate and Tris buffers should be avoided due to their potential for complexation with phenylboronic acid complexing moieties and phenylboronic acid moieties, respectively. The bioconjugate complex is formed within 1 to 15 minutes at room temperature. The reaction is insensitive to variations in ionic strength over the range 0.01 to 2 molar. Stability of the complex increases with increasing temperature, limited only by the volatility of the buffer. Addition of organic solvents including acetonitrile, methanol, ethanol, isopropanol, butanol, N,N-dimethylformamide and dimethylsulfoxide serves to further stabilize bioconjugates. Chaotropic reagents (protein denaturants) including urea, guanidine hydrochloride and formamide also serve to further stabilize bioconjugates, if and when the bioactive species is tolerant of their presence. Bioconjugate complexes may be purified by desalting, dialysis, size exclusion chromatography and electrophoresis. Bioconjugate complexes are stable upon removal of water, and can be lyophilized for storage.

Figure 8:
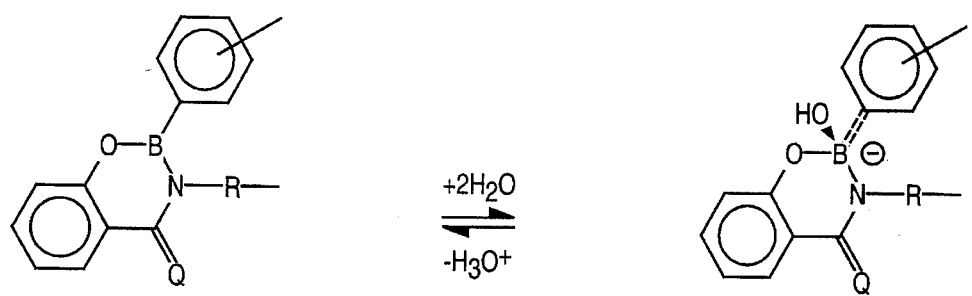
FIG. 8 illustrates both the trigonal and tetrahedral forms of bioconjugate complexes of General Formulas I to III.
Figure 9:
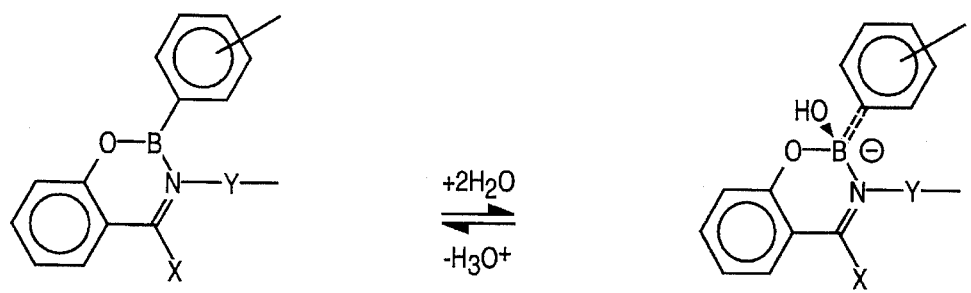
FIG. 9 illustrates both the trigonal and tetrahedral forms of bioconjugate complexes of General Formulas IV to VI.

Ionization of phenylboronic acid is an important factor in bioconjugate complex formation, in that, upon ionization boron changes from trigonal coordination (having average bond angles of 120° and average bond lengths of 1.37 Å) to the tetrahedrally coordinated anion (having average bond angles of 109° and average bond lengths of 1.48 Å). FIGS. 8 and 9 illustrates both the trigonal and tetrahedral forms of bioconjugate complexes of General Formulas I and IV, respectively.

Phenylboronic acids vary in $pK_a$ between approximately 5.2 and 9.2. Bioconjugate complexes of General Formulas I, III, IV and VI, derived from (4-carboxyphenyl)boronic acid, have approximate $pK_a$ values in the range 6.5 to 7.5. Bioconjugate complexes of General Formulas I, II, IV and V, derived from (3-aminophenyl)boronic acid, have approximate $pK_a$ values in the range 8.0 to 9.0. Complexes of General Formulas I, II, IV and V derived, from either (3-amino-2-nitrophenyl)boronic acid, (3-amino-5-nitrophenyl)boronic acid, and (3-amino-6-nitrophenyl)boronic acid have intermediate $pK_a$ values. As a general rule, the $pK_a$ of a complex of General Formulas I through VI is approximately one pH unit below that of the phenylboronic acid from which the complex was prepared.

Figure 10:
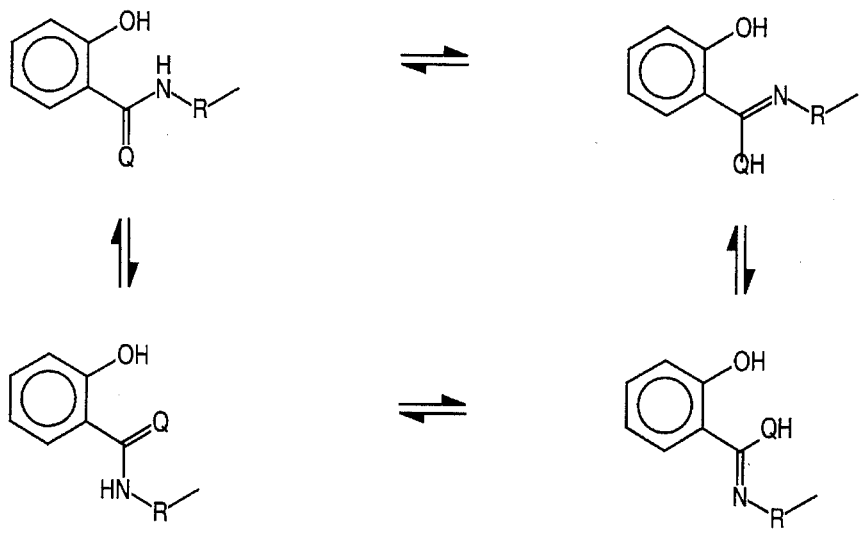
FIG. 10 illustrates tautomeric and conformational isomers of semiconjugates derived from reagents of General Formulas I to III.
Figure 11:
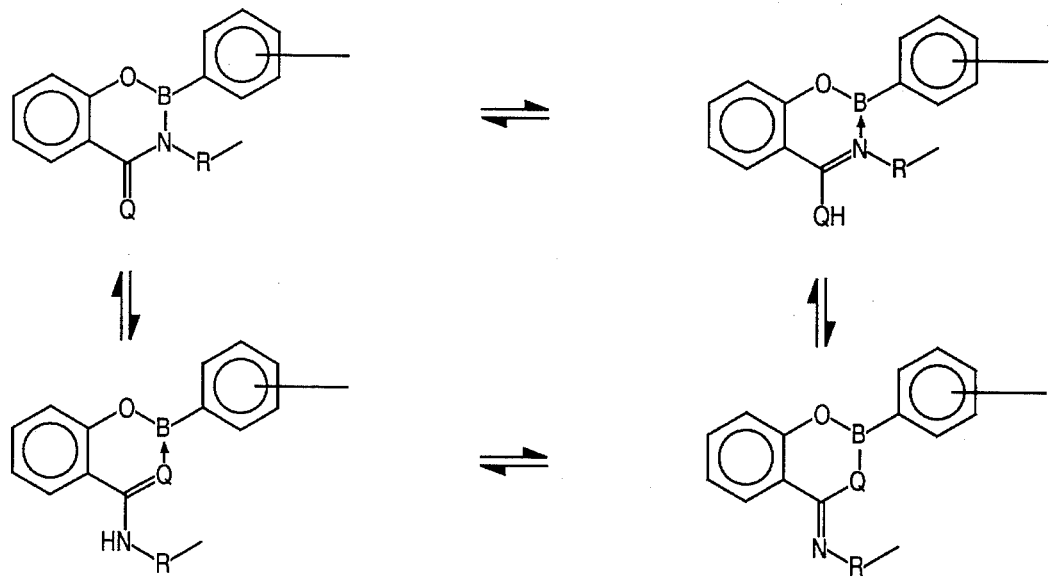
FIG. 11 illustrates tautomeric and conformation isomers of bioconjugates complexes of General Formulas I to III.

For each phenylboronic acid moiety, the stability of the bioconjugate complex, at a given pH, is determined by the substituent groups, either Q and R, for bioconjugate complexes of General Formulas I, II and III, or X and Y, for bioconjugate complexes of General Formulas IV, V and VI, respectively. For semiconjugates derived from reagents of General Formula VII, individuals skilled in the art will recognize that a number of tautomeric and conformational isomers exist in equilibrium, as illustrated in FIG. 10. Each of the isomers depicted in FIG. 10 may contribute to the phenylboronic acid complex, as illustrated in FIG. 11.

Bioconjugate Complex Formation pH Considerations

Bioconjugate complexes of General Formulas I, II and III, wherein group Q is preferably selected from either O, S and NH, wherein group R is preferably selected from either O and NH, and wherein the phenylboronic acid moiety is derived from (3-aminophenyl)boronic acid, are stable in buffered alkaline aqueous solutions over the approximate pH range 8.5 to 11.5. Similarly, bioconjugate complexes of General Formulas IV, V and VI, wherein group X is preferably selected from either H, $CH_2$ and $C_6H_5$, wherein group Y is preferably selected from either O and NH, and wherein the phenylboronic acid moiety is derived from (3-aminophenyl)boronic acid, are stable in buffered alkaline aqueous solutions over the approximate pH range 8.5 to 11.5. This range of pH stability results from the requirement that only the phenylboronate anion affords a stable complex. Nevertheless, above pH 11.5 the complex is unstable, due to base catalyzed hydrolysis. Bioconjugate complexes which exhibit stability only under alkaline conditions are useful for reversible conjugation, whereby the bioconjugate complex may be disassociated by appropriate adjustment of the pH.

Bioconjugate complexes of General Formulas I, II and III, wherein both groups Q and R are preferably 0, and wherein the phenylboronic acid moiety is derived from either (3-aminophenyl)boronic acid and (4-carboxyphenyl)boronic acid, constitute a special case in which complexes are stable in buffered aqueous solutions over the broad approximate pH range 2.5 to 11.5. This wide range of pH stability is thought to result from the presence of a coplanar 1,3-diol complexing moiety associated with the enol form of the 2-hydroxybenzohydroxamic acid moiety. Alternatively, pH stability may result from the low effective $pK_a$ of the phenylboronic acid in the complex which results from reaction of a hydroxamic acid anion ($CON^-OH$) with phenylboronic acid forming a dative bond which fills the outer electron shell of the boron atom. Bioconjugate complexes of this type form in an essentially irreversible manner, as they may only be disassociated by adjustment of the pH to above 11.5, or below 2.5, or by competitive dissociation with borate buffer.

Characterization of Semiconjugates

Semiconjugates prepared as illustrated in FIG. 1, wherein the bioactive species is a protein, may be characterized with respect to the number of pendant phenylboronic acid complexing moieties incorporated (degree of substitution) per protein molecule. Semiconjugates are characterized by reaction with an excess of a fluorescent phenylboronic acid reagent, in a buffered aqueous solution of appropriate pH, to afford a bioconjugate complex of General Formula XII, wherein Q, R, Z, Z* and BAS are as were previously defined, and wherein a fluorescent moiety F* is the bioactive species.

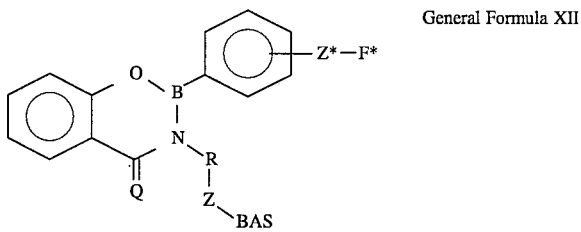

General Formula XII

Similarly, semiconjugates prepared as illustrated in FIG. 4, wherein the bioactive species is a protein, may be characterized with respect to the number of pendant phenylboronic acid complexing moieties by reaction with an excess or a fluorescent phenylboronic acid reagent, in a buffered aqueous solution of appropriate pH, to afford a bioconjugate complex of General Formula XIII, wherein X, Y, Z, Z* and BAS are as were previously defined, and wherein a fluorescent moiety F* is the bioactive species.

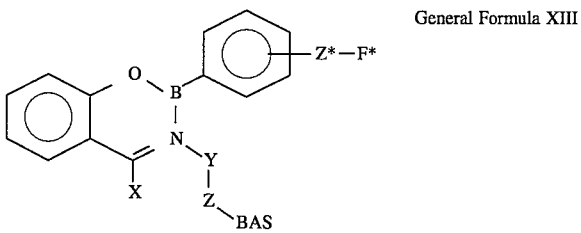

General Formula XIII

Similarly, semiconjugates having pendant phenylboronic acid moieties may be characterized by reaction with an excess of a fluorescent phenylboronic acid complexing reagent, in a buffered aqueous solution of appropriate pH, to afford bioconjugate complexes of either General Formula XIV, wherein Q, R, Z, Z* and BAS* are as were previously defined, and wherein a fluorescent moiety F is the bioactive species, or General Formula XV, wherein X, Y, Z, Z* and BAS* are as were previously defined, and wherein a fluorescent moiety F is the bioactive species.

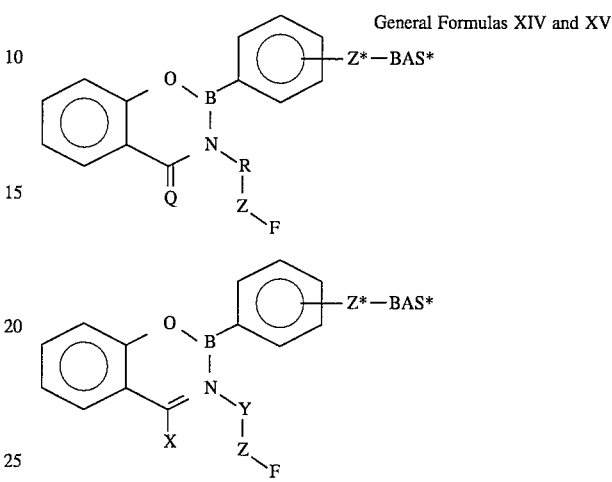

General Formulas XIV and XV

The fluorescent moieties F* and F are preferably selected from, but not limited to, either fluorescein, rhodamine X, tetramethylrhodamine, Texas Red, phycoerythrin and allophycocyanin. After removal of the excess reagent by desalting, dialysis or size exclusion chromatography, the bioconjugate complex of either General Formula XII, General Formula XIII, General Formula XIV and General Formula XV is subjected to spectroscopic analysis, and the number of phenylboronic acid complexing moieties or phenylboronic acid moieties, calculated by comparing the ratio of the absorption at 280 nm, which denotes the total protein concentration, to the absorption at a wavelength characteristic of the fluorophore ($\lambda_{max}$).

The preparation of a single fluorescent phenylboronic acid, for use as a cell surface glycoprotein labeling reagent, has been previously reported (Burnett, T. J., Peebles, H. C. and Hageman, J. H. (1980) *Biochem. Biophys. Research Commun.*, 96, 157–162).

Semiconjugates derived from other high molecular weight bioactive species which are suitable for purification by desalting, dialysis or size exclusion chromatography may be characterized in an analagous manner.

EXAMPLE I

Preparation of An Amine Reactive Reagent of General Formula VIII
N-(3-Dihydroxyborylphenyl)succinamic Acid, Succinimidyl Ester Succinic anhydride (5.00 grams, 0.05 mole) and (3-aminophenyl)boronic acid (7.75 grams, 0.05 mole) are dissolved in anhydrous pyridine (40 ml), and then allowed to stand overnight at room temperature. Water (20 ml) is added and the resulting solution allowed to stand for 1 hour. The product is then concentrated on a rotary evaporator at 85°–90° C. The resulting aqueous solution is Frozen in a dry-ice-acetone-slurry and lyophilized overnight. The lyophilized product is dissolved in water (50 ml) and acidified with concentrated HCl to approximately pH 1.0. The acidified solution is cooled in an ice bath for 1 hour, and the precipitate collected by filtration. The precipitate is recrystallized from boiling water (200 ml) and dried overnight in vacuo over NaOH pellets, to afford 8.60 grams (70% yield) of N-(3-dihydroxyborylphenyl)succinamic acid. Homogeneous by TLC (CHCl$_3$/CH$_3$OH/CH$_3$COOH; 60:35:5), R$_f$=0.5. Melting point 186°–188° C. The structure was confirmed by 300 MHz, $^1$H NMR spectrometry in d$_6$-DMSO.

N-(3-dihydroxyborylphenyl)succinamic acid (16.0 grams, 0.063 mole) is dissolved in dry DMF (80 ml). To the solution is added N,N-dicyclohexylcarbodiimide (14.3 grams, 0.069 mole) followed by N-hydroxysuccinimide (8.05 grams, 0.070 mole). The reaction is stirred overnight at room temperature. N,N-Dicyclohexylurea is filtered from the solution, and the filtrate extracted with ethyl acetate (200 ml). The extract is washed with water (3×400 ml) and saturated NaCl (400 ml). The water wash was back-extracted with ethyl acetate (200 ml), the extracts combined, dried over anhydrous Na$_2$SO$_4$, and concentrated on a rotary evaporator to afford 12.5 grams (57% yield)of N-(3-dihydroxyboryl-phenyl)succinamic acid, succinimidyl ester. Purity estimated at 98% by TLC (CHCl$_3$/CH$_3$OH/CH$_3$COOH; 85:10:5), R$_f$=0.7. The structure was confirmed by 300 MHz, $^1$H NMR, spectrometry in d$_6$-DMSO.

EXAMPLE II

Applications of An Amine Reactive Reagent of General Formula VIII

Proteins may be modified with amine reactive phenylboronic acid reagents of General Formula VIII by reaction with the side-chain ε-amino groups of lysine residues, to afford semiconjugates having pendant phenylboronic acid moieties covalently affixed to the protein through stable amide bonds. N,N-Dimethylformamide and dimethylsulfoxide are the solvents of choice. Mildly alkaline aqueous buffers, in the pH range 7.8 to 8.8, and preferably 100 mM bicarbonate buffer, pH 8.2, should be employed so as to insure that the amino group is unprotonated, while minimizing hydrolysis of the N-hydroxysuccinimidyl ester. Activated N-hydroxysuccinimidyl esters have been observed to interact with phenylboronic acids in alkaline aqueous solutions resulting in a significant reduction in their reactivity. To overcome this limitation, aqueous reactions involving N-(3-dihydroxyborylphenyl)succinamic acid, succinimidyl ester should only be undertaken in the presence of at least a 10-fold molar excess of a phenylboronic acid complexing ligand. Compounds found to be useful in this regard include mannitol and catechol. Phenylboronate complexes temporarily prepared for this purpose may be readily dissociated upon neutralization of the solution. Primary amine containing buffers including Tris and glycine must be avoided, due to their potential reactivity. Solid-phase supports having pendant primary amine moieties, including blotting membranes and microtiter plates, may be functionalized by reaction with phenylboronic acid reagents of General Formula VIII to afford solid-phase supports having pendant phenylboronic acid moieties.

EXAMPLE III

Preparation of A Thiol Reactive Reagent of General Formula VIII (3-Maleimidophenyl)boronic Acid Ethyl acetate (400 ml) is cooled in an ice bath to approximately 0° C. Maleimide (7.76 grams,) is added to the cooled solvent with stirring, followed by N-ethylmorpholine (10.19 ml). Methyl chloroformate (6.26 ml,) is added dropwise from an addition funnel at an appropriate rate so as to maintain the temperature of the reaction below 3° C. After completion of the addition, the reaction is stirred for an additional 30 min. while maintaining the temperature below 3° C. The resulting mixture is filtered through a Buchner funnel, and the precipitate washed with a small volume of ethyl acetate. The filtrate and wash are combined, and then washed with ice cold water (100 ml). The organic phase is dried over anhydrous Na$_2$SO$_4$, and then concentrated on a rotary evaporator. The product is dissolved in a mixture of ethyl acetate and isopropyl ether (40:60 v/v, 75 ml) in a water bath at 60° C., and then allowed to recrystallize at room temperature. Crystals of N-methoxycarbonylmaleimide are washed with isopropyl ether (2×20 ml), and then dried overnight in vacuo.

(3-Aminophenyl)boronic acid (1.26 grams, 0.01 mole) is dissolved in saturated NaHCO$_3$ (50 ml) by briefly heating the mixture on a hot plate. The solution is cooled in an ice bath to approximately 0° C., and N-methoxycarbonylmaleimide (1.55 grams, 0.01 mole) added with vigorous stirring. After 10 min. the solution is diluted with water (200 ml) and then stirred at room temperature for 30 to 40 min. The pH is adjusted to approximately 5.5 by addition of 1M H$_2$SO$_4$, and the precipitate collected by filtration. The precipitate is washed with 1M H$_2$SO$_4$ (2×50 ml), and then dried overnight in vacuo over NaOH pellets to afford 1.39 grams (64% yield) of (3-maleimidophenyl)boronic acid. The structure was confirmed by 300 MHz, $^1$H NMR spectrometry in d$_6$-DMSO.

EXAMPLE IV

Applications of A Thiol Reactive Reagent of General Formula VIII

Proteins containing disulfide bonds (cystine residues) or cysteine residues may be modified with thiol reactive phenylboronic acid reagents of General Formula VIII. Disulfide bonds are first reduced, if required, by reaction with 2-mercaptoethanol or dithiothreitol, in an alkaline aqueous buffer. The excess reducing reagent is removed by dialysis or desalting, and the protein reacted with (3-maleimidophenyl)boronic acid in 25 to 100 mM phosphate buffer, pH 7.0 to 7.5, for 1 hour at 4° C., to afford a semiconjugate having pendant phenylboronic acid moieties covalently affixed to the protein. Proteins which lack thiol moieties may be functionalized by reaction with a thiolating reagent, and then modified as described above. Thiolating reagents which have proven useful for this purpose include N-hydroxysuccinimidyl 3-(2-pyridyldithio)propionate, N-hydroxy-succinimidyl S-acetylthioacetate and 2-iminothiolane.

EXAMPLE V

Preparation of An Aldehyde Reactive Reagent of General Formula VIII
N-(3-Dihydroxyborylphenyl)succinamic Acid Hydrazide Methanol (10 ml) is cooled in an ice bath to approximately 0° C., and thionyl chloride (1 ml) slowly added. To the resulting stirred solution is added N-(3-dihydroxyborylphenyl)-succinamic acid (1.25 grams, 0.005 mole), prepared as described in Example 1, and the reaction is stirred overnight at room temperature. The solution is concentrated on a rotary evaporator to afford a white crystalline material which is coevaporated twice from methanol (2×10 ml) to remove residual thionyl chloride. The product is dissolved in methanol (5 ml) and hydrazine hydrate (1 ml) added. The resulting solution is stirred overnight at room temperature. A precipitate forms within a few hours. The precipitate is collected by filtration, washed with cold methanol and dried overnight in vacuo over NaOH pellets to afford 1.11 grams (88% yield) of N-(3-dihydroxyborylphenyl)succinamic acid hydrazide. The structure was confirmed by 300 MHz, $^1$H NMR spectrometry in $d_6$-DMSO.

EXAMPLE VI

Application of An Aldehyde Reactive Reagent of General Formula VIII

Glycoproteins, and particularly antibodies, may be conjugated with an aldehyde reactive phenylboronic acid hydrazide reagent after treatment of the protein with from 5 to 20 mM sodium meta periodate (NaIO$_4$), in from 0.1 to 0.5M sodium acetate buffer at pH 5 to 6, containing up to 0.2M sodium chloride, at 0° C., for from 30 minutes to 4 hours. The excess periodate is removed by desalting, and the activated protein, having pendant adjacent aldehyde moieties resulting from periodate oxidation of carbohydrate residues having 1,2-diol moieties, is condensed with the hydrazide reagent, for from 1 to 24 hours at room temperature, to afford a semiconjugate having pendant phenylboronic acid moieties covalently appended to the protein through a Schiff base (an imine) type linkage. The stability of the linkage to the protein may be increased, if desired, by mild sodium cyanoborohydride reduction of the Schiff base to the corresponding alkylamine.

It is important to note that periodate oxidation of a glycoprotein activates the protein toward reaction with a hydrazide type reagent while simultaneously removing most naturally occurring phenylboronic acid complexing moieties (coaxial 1,2-diols) associated with glycoproteins.

I claim:

1. A phenylboronic acid bioconjugate of the General Formula I

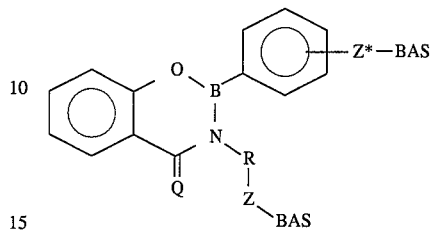

General Formula I wherein group Q is selected from O, S, NH, and N-alkyl, and wherein alkyl denotes an alkyl hydrocarbon moiety, wherein group R is selected from O, NH, CH$_2$, and alkyl, and wherein alkyl denotes an alkyl hydrocarbon moiety of from 2 to 6 carbons in length, wherein groups Z and Z*, may be the same or different and are selected from an alkyl chain of from 1 to 16 carbon equivalents in length, and wherein groups BAS and BAS* are bioactive species.

2. The phenylboronic acid bioconjugate of claim 1:

wherein group Q is selected from O and NH, wherein group R is selected from O and CH$_2$, wherein groups Z and Z* are (CH$_2$)n, wherein n=1 to 5.

* * * * *